United States Patent [19]

Freeman et al.

[11] Patent Number: 6,060,079
[45] Date of Patent: May 9, 2000

[54] DEVICE FOR TOPICAL LOCALIZED ADMINISTRATION OF ZINC TO TISSUE

[76] Inventors: Frank Freeman, Ekali, Hope Town, Elbow Cay Island, Abaco, Bahamas; Peter Sheehan, 190 Garfield Pl., Brooklyn, N.Y. 11215

[21] Appl. No.: 09/149,967

[22] Filed: Sep. 9, 1998

[51] Int. Cl.⁷ ..................................................... A61F 13/00
[52] U.S. Cl. ......................... 424/449; 424/447; 424/642; 602/48
[58] Field of Search .................... 424/642, 443, 424/447, 449; 602/42, 43, 48, 52, 59

[56] References Cited

U.S. PATENT DOCUMENTS

| | | | |
|---|---|---|---|
| 2,344,830 | 3/1944 | Mohs | 167/63 |
| 4,022,880 | 5/1977 | Vinson et al. | 424/49 |
| 4,160,821 | 7/1979 | Sipos | 424/49 |
| 4,229,437 | 10/1980 | Likens et al. | 424/145 |
| 4,315,916 | 2/1982 | Likens et al. | 424/145 |
| 4,335,110 | 6/1982 | Collins | 424/145 |
| 4,341,207 | 7/1982 | Steer et al. | 128/155 |
| 4,517,172 | 5/1985 | Southard | 424/7.1 |
| 4,538,603 | 9/1985 | Pawelchak et al. | 128/156 |
| 4,544,761 | 10/1985 | Taylor et al. | 556/130 |
| 4,551,490 | 11/1985 | Doyle et al. | 524/22 |
| 4,773,409 | 9/1988 | Cilento et al. | 128/156 |
| 4,847,083 | 7/1989 | Clark | 424/642 |
| 4,876,278 | 10/1989 | Taylor et al. | 514/494 |
| 4,895,727 | 1/1990 | Allen | 424/642 |
| 4,909,243 | 3/1990 | Frank et al. | 602/58 |
| 5,079,010 | 1/1992 | Natterer | 424/617 |
| 5,708,023 | 1/1998 | Modak et al. | 514/494 |

FOREIGN PATENT DOCUMENTS

2141929  1/1985  United Kingdom .

OTHER PUBLICATIONS

Mohs, F.E., "Chemosurgery in Cancer, Gangrene and Infections", Charles C. Thomas, Springfield, IL, 1956, p. 317.

Bailin, P.L.; "Mohs' Chemosurgery for the Treatment of Cutaneous Gangrene"; CUTIS, vol. 21: 476–478, Apr. 1978.

Falanga, V., et al.; "Zinc Chloride Paste for the Debridement of Chronic Leg Ulcers"; *Dermatol Surg Oncol*, 16:7 Jul. 1990.

*Primary Examiner*—Robert H. Harrison
*Attorney, Agent, or Firm*—Marvin S. Aronoff

[57] ABSTRACT

A device is provided for the topical localized administration of zinc to tissue. The device comprises a central layer of absorbent material, with the central layer containing a mixture of particulate superabsorbent and zinc chloride that is sandwiched between a first and second layer of perforated polymeric film that is sealed at the edges. The device is activated by exposure to aqueous media prior to application to tissue. The quantity of zinc chloride contained in the device is varied according to the intended use. High levels of zinc chloride are used to form more concentrated solutions or gels for fixation of necrotic, gangrenous or cancerous tissue to facilitate excision or amputation while lower levels are used for more dilute solutions or gels to promote formation of granulation tissue and healing of lesions in non-necrotic tissue. The device is wrapped on the site to be treated or attached by adhesive means and is kept in place for a period appropriate to the intended use.

10 Claims, 1 Drawing Sheet

6,060,079

DEVICE FOR TOPICAL LOCALIZED ADMINISTRATION OF ZINC TO TISSUE

BACKGROUND OF THE INVENTION

This invention deals with improvements in the therapeutic topical application of zinc compounds to tissue and most particularly the application of zinc chloride as a fixative for necrotic, gangrenous and cancerous tissue to facilitate excision or amputation and also to promote healing of wounds.

Chemosurgery is a method of chemical fixation of diseased tissue followed by controlled surgical removal. Zinc chloride ($ZnCl_2$) has long been used in medicine as a means to fix necrotic tissue to facilitate excision and amputation. This method has been in existence for over 50 years and its use has been best documented by Mohs application to cancers of the skin and gangrene. This work has been largely summarized in Mohs, FE, *Chemosurgery in Cancer, Gangrene and Infections*, Charles C. Thomas, Springfield, Ill., 1956 which is herein incorporated by reference to the extent that it is pertinent. Diabetic patients, for example, are among those afflicted with gangrene which may necessitate the amputation of toes fingers and limbs. Such amputations using conventional operating room procedures are often extremely expensive. Mohs in U.S. Pat. No. 2,344,830, which is herein incorporated by reference, disclosed paste formulations to control the area and depth of penetration of $ZnCl_2$ in fixing tissue prior to excision. Although an improvement over procedures generally in use at the time, control of the depth of penetration and the area exposed to the $ZnCl_2$, which are critical factors, is still difficult with Mohs' preparations. Confounding variables of skin contour, adjacent tissues and even ambient temperature and humidity contribute to the difficulty in controlling this procedure. Seepage of these preparations through wound dressings can also unintentionally expose healthy tissue of either the subject or treating provider to the fixative action of $ZnCl_2$ thereby resulting in injury.

There is therefore a need for a means to more precisely control the area of tissue exposed and the depth of penetration in the topical application of high concentrations of $ZnCl_2$ and a convenient and effective means to apply it to a target area and confine its activity to the desired target area without damaging healthy tissue. There is a further need for a relatively inexpensive means to facilitate amputation of gangrenous and necrotic tissue when necessary, without subjecting the patient to the trauma and expense of major surgery in an operating room setting. It has, however, been clinically observed that relatively low concentrations of zinc chloride, which penetrates the skin relatively rapidly, promotes rapid wound healing by accelerating the generation of granulation tissue even in the case of severe lesions such as those resulting from amputation. The beneficial action of zinc compounds such as zinc oxide in promoting the healing of skin lesions and wounds is well known. However, the beneficial wound healing properties of zinc oxide are limited by its slow penetration into the skin. There is yet a still further need for a means to topically administer zinc chloride in low concentrations in a manner that will promote the formation of granulation tissue and promote wound healing.

BRIEF DESCRIPTION OF THE INVENTION

The present invention is directed to meeting the foregoing needs by providing a means of topically applying $ZnCl_2$ that enables more precise control of the tissue area exposed to this agent and the depth of its penetration into the tissue, and also effectively confines its activity to the targeted area, thereby facilitating excision and amputation of gangrenous and necrotic tissue outside of the operating room setting. In addition, the present invention facilitates the controlled administration of zinc chloride in amounts that are effective in promoting the formation of granulation tissue thereby accelerating wound healing. These objectives are achieved by means of a skin contacting device comprising a polymeric web containing zinc chloride mixed with a super absorbent that is laminated on both sides with a suitable microperforated plastic film or a suitable plastic film which is subsequently perforated. The final web is cut and sealed into suitable shapes and sizes by standard means known in the art.

The product is activated by spraying with saline or water by prior immersion in water or by other exposure to aqueous media before winding around the gangrenous digit.

DESCRIPTION OF THE PREFERRED EMBODIMENTS

Figure 1:
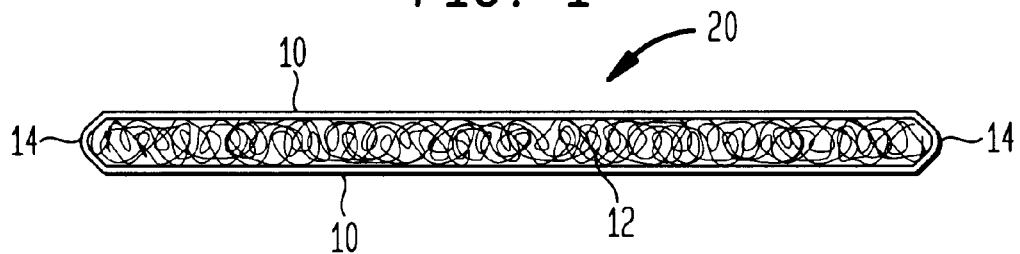
FIG. 1 is a cross-sectional view of an embodiment of the device of the present invention having a central layer comprising fibers containing a superabsorbent intermixed with zinc chloride and a top and bottom film layer comprising perforated films that are sealed to each other on the ends and sides.
Figure 2:
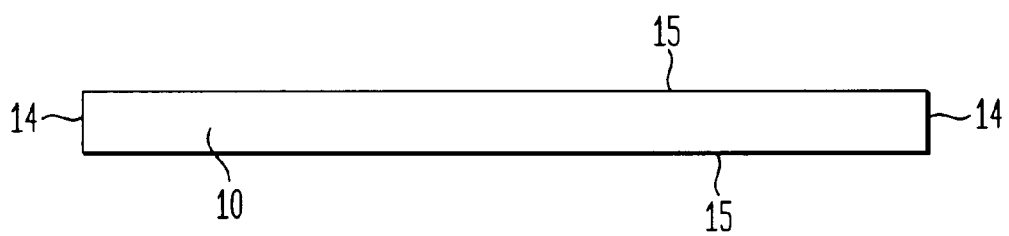
FIG. 2 is a top view of the embodiment of the device of the present invention depicted in FIG. 1.

FIG. 1 is a cross-sectional view of an embodiment of the device 20 of the present invention having a central layer or core comprising an absorbent material, typically a fibrous web, 12 containing a superabsorbent intermixed with zinc chloride and a top and bottom layer 10 comprising perforated or microporous films that are sealed to each other on the ends 14 and sides. FIG. 2 is a top view of an embodiment of device 20 depicting perforated or microporous film 10 that is a skin contact layer and end seals 14 which seal the top and bottom layers of perforated film 10 to each other at the ends of the embodiment of device 20 to form substantially water tight seals and side seals 15 which seal the top and bottom layers of perforated film 10 to each other along the sides of the embodiment of device 20 to form substantially water tight seals.

Figure 3:
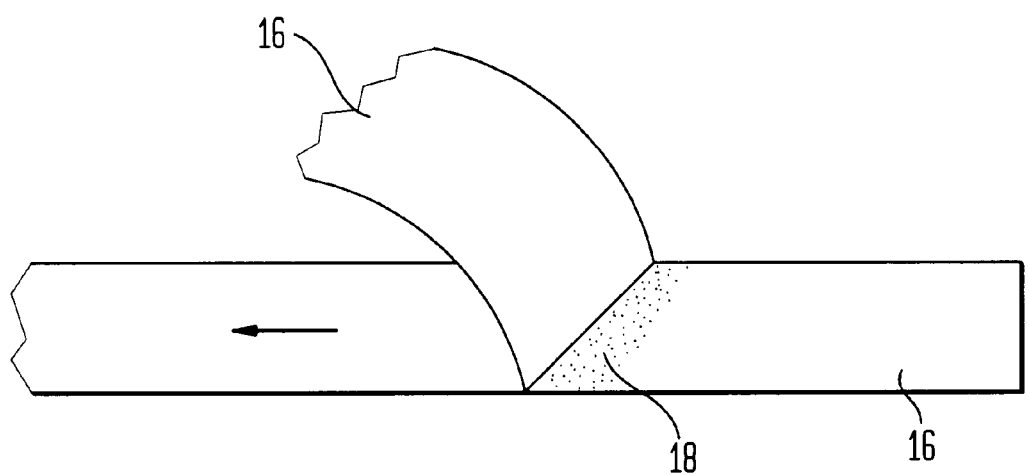
FIG. 3 is a schematic depiction of the formation of the central layer of the embodiment of the device of the present invention depicted in FIG. 1 showing a superabsorbent and $ZnCl_2$ mixture deposited on a layer of a fibrous web which is then covered by a second layer of fibrous web and calandered.

FIG. 3 schematically depicts formation of central layer 12 of an embodiment of device 20 showing a superabsorbant and $ZnCl_2$ mixture 18 deposited on a layer of a fibrous web 16 which is then covered by a second layer of fibrous web 16 and sent through calandering rolls in the direction indicated by the arrow.

Top and bottom layers 10 may be selected from a range of forms such as a web, net or perforated film. Perforated or microporous films are preferred as they permit permeation of water to the zinc chloride, superabsorbent containing central layer 12 to activate the dressing and exudation of a gel comprising aqueous zinc chloride through skin contact layer 10 onto the target area on the patients skin. Top and bottom film layers 10 may comprise polyolefins and polyolefin polymers and copolymers having functional groups such as polyethylene with or without acetate moieties, e.g. ethylene vinyl acetate (EVA), polypropylene (PP), polyesters and the like. A preferred material is ethylene vinyl acetate, for example Union Carbide Natural 7 or Evatane 1020 VN5 or Evatane 1080 VNT with a vinyl acetate (VA) content of 15 to 28 percent. Preformed perforated polyethylene or polypropylene films such as those sold under the trademark Delnet by Applied Extrusion Technologies can also be used to form top and bottom layers 10. Water soluble and water swellable polymers such as polyvinyl pyrrolidine, polyvinyl alcohol and the like are also suitable for top and bottom layers 10. Water swellable and water soluble polymer films used for layers 10 that permit sufficiently rapid penetration of water to central layer 12 and exudation of the gel comprising aqueous zinc chloride need not be perforated. In general it is preferred that films comprising layers 10 are perforated to permit the entrance of water to activate the product, and permit exudation of a solution or a gel comprising zinc chloride. In some instances it may be preferable to use a combination of perforated and unperforated films for the outer layers 10 of device 20 so that for example, the skin contacting layer is perforated while the other layer of 10 is unperforated. Such perforations may be carried out before the film is attached to the central web or they may be formed during the process of laminating film 10 to central layer 12 by processes known in the art. Suitable films may have a wide range of thickness ranging from about 0.5 mil to about 3 mil.

The web comprising central layer 12 may be selected from a number of material forms such as fabrics, foam or fibers that are comprised of polyester and polyester copolymers, polypropylene and polypropylene copolymers and polyethylenes and polyethylene copolymers and cellulosic polymers and copolymers and derivatives thereof. Although all these material forms are generally suitable, fibrous polypropylene webs are preferred for the web comprising central layer 12 as they are relatively inexpensive, readily available and easily processed. Central web 10 is further comprised of natural and synthetic polymeric absorbents and superabsorbents. Suitable absorbents and superabsorbents for aqueous media include those derived from starch grafted copolymers of acrylic salts, acrylamide salts, polyacrylate salts and the like, known in the art and commonly available commercially. Generally, any polymeric absorbent or superabsorbant that is commercially available is suitable for use in central layer 12, however the Salasorb range of superabsorbents manufactured by Allied Colloids is preferred as they are readily available and easily processed.

The central layer further comprises zinc chloride which is mixed with the absorbent or superabsorbent to form mixture 18. It is preferred that the zinc chloride and the water absorbing component of mixture 18 be in particulate or granular form to facilitate distribution within central layer 12. Mixture 18 may comprise from about 2 percent to about 98 percent of zinc chloride by weight of the dry mixture. The preferred level of zinc chloride in mixture 18 will depend on the specific application of device 20. Mixture 18 must contain an amount of zinc chloride that is effective for the intended use. For fixation of gangrenous or necrotic tissue, zinc chloride levels of about 25 percent to about 98 percent are preferred, with zinc chloride levels above about 50 percent more preferred. For promotion of wound healing or the healing of lesions in non-necrotic tissue, zinc chloride levels of about 2% to about 35% are preferred with about 10 percent to about 20 percent more preferred. The amount of mixture 18 contained in device 20 can range from about 0.5% to about 95% of the total dry weight of device 20.

The device of the present invention may be formed by processes and techniques known and practiced in the art. For example, Freeman, in U.S. Pat. No. 5,681,579 which is herein incorporated by reference, describes lamination and sealing processes involving fibrous webs that are loaded with components such as superabsorbents. Typically, an embodiment comprising Delnet microporous film comprising polypropylene, fibrous polypropylene web and a mixture of superabsorbant and zinc chloride can be formed in the following steps: a) distributing or loading the superabsorbant zinc chloride mixture onto a first layer of fibrous polypropylene web, b) laying down a second layer of fibrous polypropylene web on top of the first layer so that the mixture is contained within the two layers of web, calendering or otherwise compressing the web, c) needle punching the web, d) laminating a first layer of Delnet film to the top of the fibrous web using adhesive or thermal means and a second layer of Delnet film to the bottom of the fibrous web using adhesive or thermal means, to form a laminate having a top and bottom film layer and a central layer comprising a fibrous web containing a mixture of superabsorbant and zinc chloride e) cutting the laminate into desired lengths and widths and shapes and simultaneously or subsequently sealing the edges by ultrasonic or other means known in the art. In the case of polypropylene webs and Delnet films ultrasonic sealing is preferred. In this case the final web is cut and sealed into suitable shapes and sizes by means of ultrasonic techniques. Other techniques such as adhesive means or conventional heat sealing and others known in the art may be preferable, as is known in the art, depending on the specific combinations of materials used. The laminates of the present invention can be cut and sealed and also shaped and formed by any means known in the art to form shapes and sizes individualized to the appropriate area of the skin to be treated or, for example, to receive digits and limbs.

The preferred shape for toes and fingers is a narrow strip where the perimeter has been cut and sealed. This shape is wound around the gangrenous digit and secured in place by tying or the use of adhesive tape. In some instances where a degree of occlusiveness is useful either the first or second layer of porous film in step d) may be replaced with non-porous film. The product is activated prior to application on a patient by spraying with saline or water or by prior immersion in water. This allows the zinc chloride to be transferred to a specific area of the skin to act as a fixative in a safe and controlled manner. The concentration of the zinc chloride delivered to the tissue can be modulated by the concentration of zinc chloride in the central layer of the device or by the duration of the application time, or both. The device is utilized according to the disease state of the skin: cancers of the skin and gangrene require delivery of high concentrations of zinc chloride for its fixative properties, while inflammatory conditions, such as chronic wounds, burns and dermatoses, require low concentrations for its salutary effect on healing and granulation.

For areas that have an overlying surface of intact skin or eschar, a keratinolytic agent such as dichloroacetic acid or other agent known in the art should be used. In the case of tissue fixation such as a gangrenous digit, the digit is first treated with a keratinolytic agent such as dichloroacetic acid according to procedures known in the art and then the sprayed or wetted device is wound around the gangrenous digit. The gangrenous digit may be removed within about 24 hours with limited surgical intervention which may be performed in an ambulatory setting. In the case of open lesions or wounds the device or wound dressing of the present invention containing an effective amount of zinc chloride is applied to the area of the lesion and held in place by adhesive means. The lesion is examined periodically for the development of granulation tissue and replaced as needed if necessary.

Although the present invention has been described in considerable detail with reference to certain preferred versions thereof, other versions are possible. Therefore, the spirit and scope of the appended claims should not be limited to the description of the preferred versions contained herein.

What is claimed is:

1. A device for the topical localized administration of zinc to tissue with the device activated by applications of aqueous media and with the device comprising:

a first layer of film having perforations and, a second layer of film having perforations and, a central layer of absorbent material, with the central layer containing;

a mixture of particulate absorbent and zinc chloride and; with the central layer sandwiched between the first layer and the second layer of film to form a sandwich having edges and with the edges sealed so that the sealed edges are substantially water tight so that the activating aqueous media can enter the device substantially only via the perforations of the perforated film with the activating aqueous media that enters the device forming an aqueous solution or gel comprising zinc chloride with the zinc chloride contained in the central layer and with the particulate absorbent in the central layer absorbing a portion of the aqueous media and with the aqueous solution or gel comprising zinc chloride exuding substantially only through the perforations of the perforated films to topically administer the solution or gel comprising zinc chloride to the tissue.

2. The device of claim 1 wherein the central layer of absorbent material comprises at least one material in a form selected from the group consisting of foam, fabric, fibers and web.

3. The device of claim 2 wherein the central layer of absorbent material contains an effective amount of zinc chloride for tissue fixation and a polymeric superabsorbent.

4. The device of claim 2 wherein the central layer of absorbent material contains an effective amount of zinc chloride for the development of granulation tissue in a lesion and a polymeric superabsorbent.

5. The device of claim 3 wherein the central layer comprises a material selected from the group consisting of polyolefins, polyesters, cellulosic materials and mixtures thereof.

6. The device of claim 4 wherein the central layer of absorbent material comprises a material selected from the group consisting of polyolefins, polyesters, cellulosic materials and mixtures thereof.

7. The device of claim 5 wherein the central layer of absorbent material comprises two plies of a fibrous web with the superabsorbant zinc chloride mixture sandwiched between the plies of the web.

8. The device of claim 6 wherein the central layer of absorbent material comprises two plies of a fibrous web with the superabsorbant zinc chloride mixture sandwiched between the plies of the web.

9. The device of claim 1 wherein the first layer of film and the second layer of film have a thickness of about 0.5 mil to about 3 mil.

10. The device of claim 1 wherein a one of the first layer of film and the second layer of film is unperforated and the aqueous solution or gel comprising zinc chloride exudes substantially only through the perforations of the perforated film.

* * * * *